United States Patent [19]

Doonan et al.

[11] 3,958,938
[45] May 25, 1976

[54] BIOLUMINESCENT SENSOR SYSTEM

[75] Inventors: Douglas D. Doonan, Rochester, N.Y.; Roy R. Sakaida, Woodland Hills, Calif.

[73] Assignee: Bausch & Lomb Incorporated, Rochester, N.Y.

[22] Filed: Dec. 16, 1974

[21] Appl. No.: 533,096

[52] U.S. Cl. .......................... 23/230 B; 23/253 R; 195/103.5 R; 195/127
[51] Int. Cl.² ...................... C12K 1/04; C12K 1/10; G01N 33/16
[58] Field of Search .......... 23/230 B, 253 R, 232 R; 195/127, 103.5 R; 250/361; 356/181

[56] References Cited
UNITED STATES PATENTS

| | | | |
|---|---|---|---|
| 3,359,973 | 12/1967 | Hoffman | 195/127 |
| 3,370,175 | 2/1968 | Jordon et al. | 23/232 R |
| 3,849,653 | 11/1974 | Sakaide et al. | 23/232 E X |
| 3,868,223 | 2/1975 | Robock et al. | 23/253 R |

*Primary Examiner*—Robert M. Reese
*Attorney, Agent, or Firm*—Frank C. Parker; Bernard D. Bogdon

[57] ABSTRACT

In a bioluminescent sensor system there is provided a fluid path for passing vapors across a bioluminescent microorganism sensor to momentarily test for a specific vapor and a recirculating fluid path for otherwise passing humidified air across the sensor to provide humidification to condition the sensor environment to preclude the loss of moisture from the sensor microorganism and stabilize the luminescence and response characteristics of the sensor culture.

5 Claims, 4 Drawing Figures

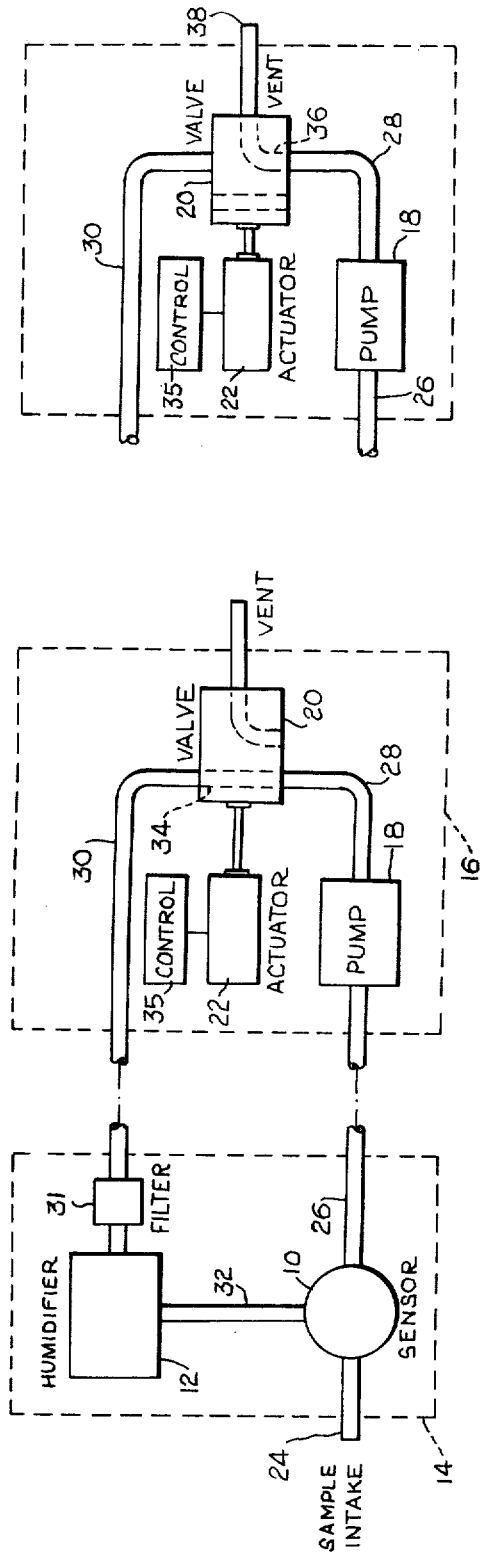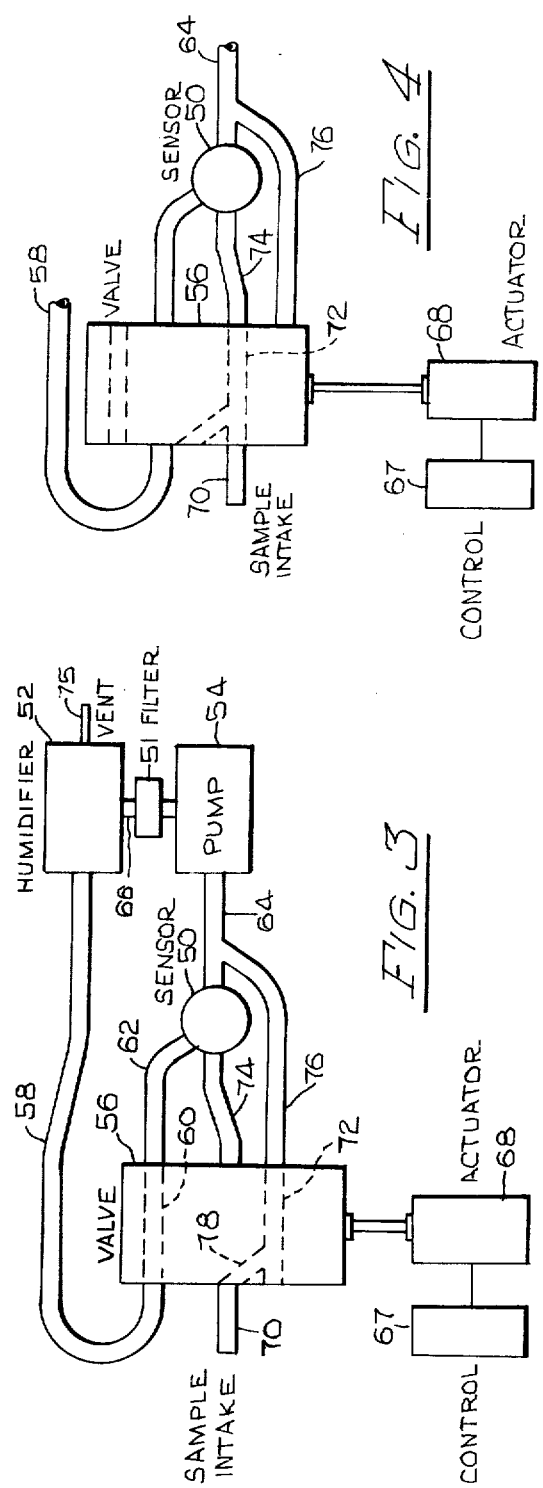

BIOLUMINESCENT SENSOR SYSTEM

BACKGROUND OF THE INVENTION

1. Field of the Invention

This invention relates to a bioluminescent sensor system and in particular to a detection system including at least one sensor for identifying specific vapors, with fluid paths for alternately introducing fluid sample for testing, and humidified fluid for conditioning the sensor and its environment.

2. Description of the Prior Art

In fluid or air sampling systems in use with bioluminescent sensors where the sensor is typically isolated, except during short sampling or humidifying intervals, such as disclosed in U.S. Pat. No. 3,370,175 entitled Toxicant Detector for inventors A. L. Jordan et al, issued on Feb. 20, 1968 and assigned to the owner of the present invention, sensitivity of the detection medium may be affected. This can be caused by a loss in moisture from the agar medium or other suitable substrate, on which the detection medium, including the luminous culture comprising microorganisms such as bacteria or fungi, are grown. Air sampling systems which provide only for sample fluid or air continuously blowing across the sensors, if not otherwise compensated for, can be the cause of unsatisfactory results since the sensor loses moisture and can respond to humidity changes, and the total luminescence and reactivity of the culture may be changed and generally decreased. Air sampling systems, where the bioluminescent sensor is constantly exposed to the atmosphere being tested, cause the sensor to become equilibrated to the specific gas under test and the biosensor will not respond to that gas unless it is above the ambient concentration.

Typical solutions to these humidification problems involve so-called stop-flow methods where the air flows across a sensor and is turned on and off at a rate dependent upon the frequency of sampling and in-line humidification where the sample passes through a humidifier. However, the first solution has drawbacks in that the bioluminescent sensor detector also responds to changes in humidity and air flow thereby disturbing it and causing it to react to disturbances other than that of the specific gas under investigation. Drawbacks with respect to the latter configuration are the loss of sample in the humidifier and the decrease of response to a specific vapor if low levels are already present in the environment.

These sensor microorganisms when cultured are grown under conditions of substantially 100% humidity. Therefore, sensor viability and sensitivity is maximum at high humidities. In addition, when subjected to varying humidity and fluid flow conditions, its response is affected.

SUMMARY OF THE INVENTION

An inventive system and method to solve these problems regarding changes in detectability of the microorganism sensors due to moisture content changes is hereby provided. The invention contemplates fluid conduit systems having operational valves, or switching apparatus including fluids or hydraulic control systems whereby a continual flow of humidified clean air passes across the surface of the bioluminescent sensor during a standby or non-test period which continual flow can be briefly interrupted during the test period to allow fluid atmosphere under test to flow and pass over the microorganism sensor to determine the presence of a specific vapor.

This type of pulse-sampling method provides for a very short time-duration pulse of test air to be presented to the sensor which will preclude any appreciable change to the bioluminescent characteristics of the detector, unless of course the specific vapor under sample is detected. During the short pulse, the moisture change or loss to the sensor is insignificant and will not affect resolution of the test results.

In application an embodiment according to the principles of this invention is suitable for use in either a single sensor system or a system where more than one sensor is contemplated, such as disclosed in U.S. Pat. No. 3,849,653 issued Nov. 19, 1974 entitled Multichannel Bioluminescent Sensors assigned to the assignee of the present invention.

BRIEF DESCRIPTION OF THE DRAWINGS

FIG. 1 is a schematic illustration of a fluid sampling system according to the principles of the present invention, illustrating a recirculative humidification mode;

FIG. 2 is an illustration of a portion of the fluid sampling system of FIG. 1, illustrating a fluid sampling mode;

FIG. 3 is an alternate embodiment of a fluid sampling system according to the principles of the present invention, illustrating a recirculative humidification mode; and FIG. 4 is an illustration of a portion of the fluid sampling system of FIG. 3, illustrating a fluid sampling mode.

DESCRIPTION OF THE PREFERRED EMBODIMENTS

In the interest of providing an improved bioluminescent sensor sampling system including elements for providing for the stabilization of the luminescence of the sensor culture, there is shown in FIGS. 1 and 2, schematic illustrations of one preferred embodiment of such a system and in FIGS. 3 and 4 illustrations of another. Frequently, it is desirable to have the actual elements of such an embodiment portable for easy maintainence and handling. Portability is particularly desirable for law enforcement and safety enforcement applications where the vapor under investigation is at variable locations. In FIG. 1, for example, a sensor assembly 10 and a humidifier 12 are schematically illustrated as being encased within a remote sensor assembly unit 14. Sensor assembly unit 14, for example, can be a hand-held unit and can be easily manipulated and of convenient size to probe and sample atmospheres in confined environments. A base assembly unit 16, which can be remotely disposed from the sensor assembly unit 14, includes a pump 18 for recirculating fluid across a bioluminescent sensor element comprising a microorganism in the sensor assembly 10. The base unit 16 also includes a suitable valve 20 which, for example, may be controlled by an actuating device 22 to assume either a first position, as illustrated in FIG. 1, for a recirculating mode to pass clean humidified air over the sensor culture or a second position, as illustrated in FIG. 2, for a sampling mode to test fluid sample from the atmosphere.

Pump 18 provides for a pressure differential to draw a fluid sample from the atmosphere through an input conduit or inlet port 24 which is in direct fluid communication with the sensor assembly 10 and the sensor culture. A fluid conduit 26 extends between the sensor assembly 10 and the pump 18. Conduit 26 constitutes the outlet port of the sensor assembly 10. The pump 18 is in fluid communication with the valve 20 through a conduit 28 defining a portion of the recirculating path which further extends through the valve 20 to and through a conduit 30 communicating with the humidifier 12 through filter 31. The humidifier 12 and the filter 31 clean, scrub and humidify the recirculating fluid which passes through a conduit 32, defining the remaining portion of the recirculating path, to directly communicate with the culture of the sensor assembly 10.

In this preferred embodiment, remote sensor assembly unit 14 may be operably disposed an appreciable distance from the base assembly unit 16 in which case it may be desirable to have, either part or all of the conduit 26 which extends between the sensor 10 and the pump 18 and the conduit 30 which extends between the humidifier 12 and the valve 20, of flexible or other suitable construction to accommodate both the possible manipulation of the remote sensor assembly unit 14 and its remote disposition from the base assembly unit 16.

As hereinbefore mentioned, FIG. 1 illustrates the recirculating mode of the sensor sampling system, where the cleansed and moisturized fluid passes through the valve 20 in a closed recirculating channel 34 internal to the valve 20. When sample selecting or testing is conducted, a separate control unit 35 provides power and signal control to an actuating assembly 22 to cause it to move the valve 20 to a position, as illustrated in FIG. 2, aligning channel 36, internal to the valve 20, with the conduit 28 passing between the pump 18 and the valve 20. This established path thereby allows some fluid to pass through an output conduit 38 to the atmosphere. The motion and resultant position of the valve 20 also closes the recirculating path back to the humidifier 12 and the sensor 10. In that the pump 18 still provides a pressure drop, atmosphere is caused to move through the sample intake tube 24 and hence to be drawn across the biosensor in sensor unit 10. The sample draw to the biosensor is caused by the action of the valve 20.

The sampling period is preferably of very short duration and usually less than 5 seconds although longer periods, for example, of a minute or more can be accommodated depending of course on the controls, the vapor being detected and the microorganism in use during the test. The short pulse of test air or atmosphere does not appreciably change the bioluminescence of the detector.

Considering the portability of the embodiment of FIG. 1, it will be appreciated that a remote control unit can be stationed in the sensor assembly unit 14 for remote control operation at the hand-held unit.

An alternate preferred embodiment of the invention is illustrated in FIGS. 3 and 4. As hereinbefore stated, an embodiment according to the principles of the disclosure of FIGS. 1 and 2 has a sensor assembly unit 14 which is operable while remotely disposed from a base assembly unit 16. Where compactness is a desirability, an embodiment according to the principles of the disclosure of FIGS. 3 and 4 is more suitable. Here, as before, a sensor 50 is similarly disposed for receiving fluid cleansed by a filter 51 and moisturized by a humidifier 52 and circulated by a pump 54 through a valve 56 defining either a recirculating path, when disposed as illustrated in FIG. 3, or a sample test path, when disposed as illustrated in FIG. 4. Humidified and cleansed air passes from the humidifier 52 through a conduit 58 to and through a closed recirculating channel 60 internal to the valve 56 to be carried through a conduit 62 to directly communicate with the culture of the sensor assembly 50. When the valve is disposed as illustrated in FIG. 3, the recirculating path is continuous and is a substantially closed loop from sensor assembly 50 through conduit 64, in communication with the pump 54, to and through conduit 66 connected directly between the pump 54 and the humidifier 52. The conduit 64 constitutes the outlet port of the sensor assembly 50. During the recirculating mode the environment of the bioluminescent microorganism of sensor assembly 50 is conditioned and the culture metabolism is stabilized by the passing of the humidified air across it.

In order to sample the atmosphere for a specific vapor, a control system unit 67, provides for an actuator 68 to move the valve 56, as illustrated in FIG. 4, to define a fluid intake path. Fluid sample for test is brought in through an input conduit 70 to pass through a closed channel 72 internal to the valve 56 to pass through sensor input conduit or inlet port 74 to come in direct fluid contact with the predetermined vapor sensitive culture in the sensor assembly 50. During the period of sampling, the pump 54 operates to draw the sample across the culture of the sensor assembly 50, and through the pump 54 and the humidifier 52 to vent it to the outside atmosphere through output vent 75. After a sample has been tested any remaining test gas is purged from the system during the recirculating mode of FIG. 3 by means of a bypass conduit 76 in fluid communication with the atmosphere through the closed internal channel 72 communicating with the sample input conduit 70 through a short channel 78 also internal to the valve 56.

The components for the two alternate embodiments, including the fluid conduit and the materials of all the elements disclosed herein are substantially similar. The sensor assemblies 10 and 50 are of like construction and each generally defines an inner chamber disposed above or about a readily replaceable microorganism element. The microorganism element is disposed within the inner chamber such that both the recirculating humidified fluid conditions the environment to preclude loss of moisture from the sensing element and the fluid sample sufficiently contacts or is exposed to the sensing element for the sensing elements to react with certainty when the specific vapor under test is present in the sampled atmosphere. In addition, in order to identify changes in the bioluminescent characteristics of the sensing element when it reacts to the presence of a specific vapor, there are included photosensitive transducers which are not illustrated but, for example, can be cadmium-sulfide photoresistive cells.

The humidifiers 12 and 52 are constructed such that they can be maintained and include a moisture retaining medium such as sterile cotton or felt which can be saturated with water, preferably purified, and be maintained at a sufficient level to keep the chamber of the humidifier near or at 100% humidity. The humidifier, in conjunction with the respective filter or a suitable scrubber, will also cleanse the air by adsorption, absorption or by reacting with the organic elements carried in the air sample. Activated charcoal comprises a suitable filter element.

The pumps 18 and 54 are of sufficient size to circulate fluid through the system but generally require very little power and can, for example, be battery operated. A small diaphragm or rotary vane pump is suitable for such embodiments. The valves 20 and 56 are illustrated as slide valves, although it will be appreciated that other valves such as a rotary valve are likewise suitable for operation in the illustrated embodiments. The actuators 22 and 68, as illustrated, are preferably electrical solenoids operable to move the valve to assume the sampling mode position as best seen in FIGS. 2 and 4. It will be appreciated that other actuators could move the valve from its sampling mode position to the recirculating mode position of FIGS. 1 and 3. Such actuators might likewise be electrical solenoids or mechanically biased springs and, in addition, it will be appreciated that the valve position may be better defined if the valves latch or detent into position.

The control units 35 and 67, for example, might comprise normally operable switches, direct solenoid drives or latching solenoids, or latching triggers with solenoid release and/or include timing elements such as electronic timers or dash pot timers for controlling the duration of the sampling period.

Successful operation of the system is dependent on having fluid tight integrity within all of the illustrated components and in the connections which extend between them. The fluid conduit is of any suitable material which, like all the other components, is of such physio chemical makeup that it will not affect the responses expected from the microorganism cultures. The material for the conduit, for example, may be Teflon, stainless steel or high density polyethylene and the conduit may be secured to the individual elements by stainless steel fittings. In the alternate embodiment of FIGS. 3 and 4, it will be appreciated that when the valve is in its recirculative position of FIG. 3 the input conduit 74 is sealed and when the valve is in the sampling mode position of FIG. 4, the bypass conduit 76 is sealed. Likewise, when bypass conduit 76 is sealed conduit 62, providing an input to sensor assembly 50, is likewise sealed.

It is claimed:

1. A bioluminescent humidification method for testing for the presence of a specific vapor in an air atmosphere, comprising the steps of:
    recirculating humidified air during a non-testing period across the surface of a bioluminescent sensor to control the humidity of the bioluminescent sensor;
    substantially interrupting the passing of humidified air across the bioluminescent sensor for a period of testing;
    passing during the period of testing air from the atmosphere to be sampled across the bioluminescent sensor for testing for the presence of a specific vapor in the air atmosphere; and then repeating the step of
    recirculating humidified air across the surface of the bioluminescent sensor to condition the bioluminescent sensor for detecting a specific vapor in the air atmosphere.

2. Apparatus for testing for the presence of a specific vapor in a fluid atmosphere being sampled, comprising:
    a bioluminescent sensor assembly having a fluid inlet port for receiving sample fluid from a fluid atmosphere and a fluid outlet port and a bioluminescent culture for responding to the specific vapor under test disposed between and in fluid communication with the respective ports;
    humidification means in fluid communication with the sensor assembly for humidifying fluid to pass across the bioluminescent culture to moisturize the culture;
    a fluid communication system including fluid conduit and single valve means for cooperatively recirculating moisturized fluid between the humidification means and the sensor assembly, or for circulating sample fluid atmosphere through the inlet port of the sensor assembly to the culture of the sensor and outward to the fluid atmosphere through the outlet port of the sensor assembly to vent the sampled fluid when testing for the specific vapor; and
    pumping means for cooperatively circulating fluid within the fluid communication system to recirculate the humidifying fluid for moisturizing the culture, to sample the fluid atmosphere and to move the fluid into contact with the culture to test for a specific vapor.

3. The apparatus as defined in claim 2, wherein the valve means has a test sample inlet in fluid communication with the atmosphere being sampled and a fluid outlet in direct fluid communication with the inlet of the valve means and the inlet port of the bioluminescent sensor assembly, the valve means additionally having a recirculative fluid path in direct communication with the humidification means and the inlet port of the sensor assembly and said apparatus further including control means for actuating the valve means to provide fluid communication either between the sensor and the humidification means through the recirculative fluid path or between the sensor and the atmosphere being sampled through the test sample inlet and the fluid outlet of the valve means.

4. The apparatus as defined in claim 2, wherein the inlet port of the bioluminescent sensor assembly is in direct fluid communication with the fluid atmosphere being sampled and the humidification means is in fluid communication with the inlet port of the sensor assembly and the valve means is connected between the outlet port of the sensor assembly and the humidification means and provides fluid communication in either a continuous loop fluid path between the inlet and the outlet ports of the sensor assembly and the humidification means to humidify the bioluminescent culture of the sensor assembly or vent the sensor assembly at the outlet port to the atmosphere when sampling fluid atmosphere through the inlet port of the sensor assembly.

5. The apparatus as defined in claim 4, wherein the valve means includes a sliding valve having a first internal fluid path for venting the sensor assembly through the outlet port to the atmosphere when sampling the fluid atmosphere through the inlet port in the sensor assembly and a second internal fluid path comprising a part of the continuous loop fluid path for humidification of the bioluminescent culture.

\* \* \* \* \*